(12) United States Patent
Muiruri

(10) Patent No.: US 9,739,466 B1
(45) Date of Patent: Aug. 22, 2017

(54) STETHOSCOPE FLASHLIGHT

(71) Applicant: Benjamin Muiruri, Westford, MA (US)

(72) Inventor: Benjamin Muiruri, Westford, MA (US)

( * ) Notice: Subject to any disclaimer, the term of this patent is extended or adjusted under 35 U.S.C. 154(b) by 121 days.

(21) Appl. No.: 14/868,742

(22) Filed: Sep. 29, 2015

(51) Int. Cl.
 *F21V 21/34* (2006.01)
 *F21V 19/00* (2006.01)
 *A61B 7/02* (2006.01)
 *A61B 1/06* (2006.01)
 *F21V 33/00* (2006.01)
 *F21W 131/20* (2006.01)
 *F21Y 101/02* (2006.01)

(52) U.S. Cl.
 CPC ............... *F21V 21/34* (2013.01); *A61B 1/06* (2013.01); *A61B 7/02* (2013.01); *F21V 19/0045* (2013.01); *F21V 33/0068* (2013.01); *F21W 2131/20* (2013.01); *F21Y 2101/02* (2013.01)

(58) Field of Classification Search
 CPC ......... A61B 1/06; A61B 7/02; F21V 19/0045; F21V 21/08; F21V 21/0885; F21V 21/34; F21V 33/0068; F21W 2131/20; F21W 2131/208
 See application file for complete search history.

(56) References Cited

U.S. PATENT DOCUMENTS

| | | | |
|---|---|---|---|
| 4,783,813 A | 11/1988 | Kempka | |
| 5,448,459 A | 9/1995 | Rogers | |
| 5,989,186 A | 11/1999 | Alatriste | |
| D438,908 S * | 3/2001 | Najmi | D20/28 |
| 6,202,784 B1 * | 3/2001 | Alatriste | A61B 1/227 181/131 |
| 6,454,045 B1 | 9/2002 | Ryan | |
| D490,923 S | 6/2004 | Costa | |
| 6,932,186 B2 * | 8/2005 | Costa | A61B 7/02 181/131 |
| 6,951,409 B2 * | 10/2005 | Hsien | B25B 23/18 362/119 |
| 7,036,627 B2 | 5/2006 | Costa | |
| 7,178,933 B1 * | 2/2007 | Chuang | B62J 6/02 362/106 |
| 7,322,135 B2 * | 1/2008 | Gulati | G09F 3/00 181/131 |
| 7,527,123 B2 | 5/2009 | Puder | |
| 8,939,251 B2 * | 1/2015 | Ting | A61B 7/02 181/131 |
| 2010/0155173 A1 | 6/2010 | Boyd | |
| 2011/0201968 A1 * | 8/2011 | Goldstein | B26B 11/008 600/586 |

* cited by examiner

*Primary Examiner* — Alan Cariaso

(57) ABSTRACT

The stethoscope flashlight is a flashlight that is mounted on the tubing near the drum of the stethoscope. The stethoscope flashlight provides supplemental light during low ambient light situations (like night time visits) to provide the medical care giver to visually evaluate the patient and readily read the patient's chart without disturbing the patient. The stethoscope flashlight comprises a stethoscope, a tube mount, and a flashlight.

10 Claims, 4 Drawing Sheets

STETHOSCOPE FLASHLIGHT

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of stethoscopes and acoustic devices that are inserted into the ear canal, more specifically, a flashlight configured for use with a stethoscope.

SUMMARY OF INVENTION

The stethoscope flashlight is a flashlight that is mounted on the tubing near the drum of the stethoscope. The stethoscope flashlight provides supplemental light during low ambient light situations (like night time visits) to allow the medical care giver to visually evaluate the patient and readily read the patient's chart without disturbing the patient.

These together with additional objects, features and advantages of the stethoscope flashlight will be readily apparent to those of ordinary skill in the art upon reading the following detailed description of the presently preferred, but nonetheless illustrative, embodiments when taken in conjunction with the accompanying drawings.

In this respect, before explaining the current embodiments of the stethoscope flashlight in detail, it is to be understood that the stethoscope flashlight is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the stethoscope flashlight.

It is therefore important that the claims be regarded as including such equivalent construction insofar as they do not depart from the spirit and scope of the stethoscope flashlight. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Figure 1:
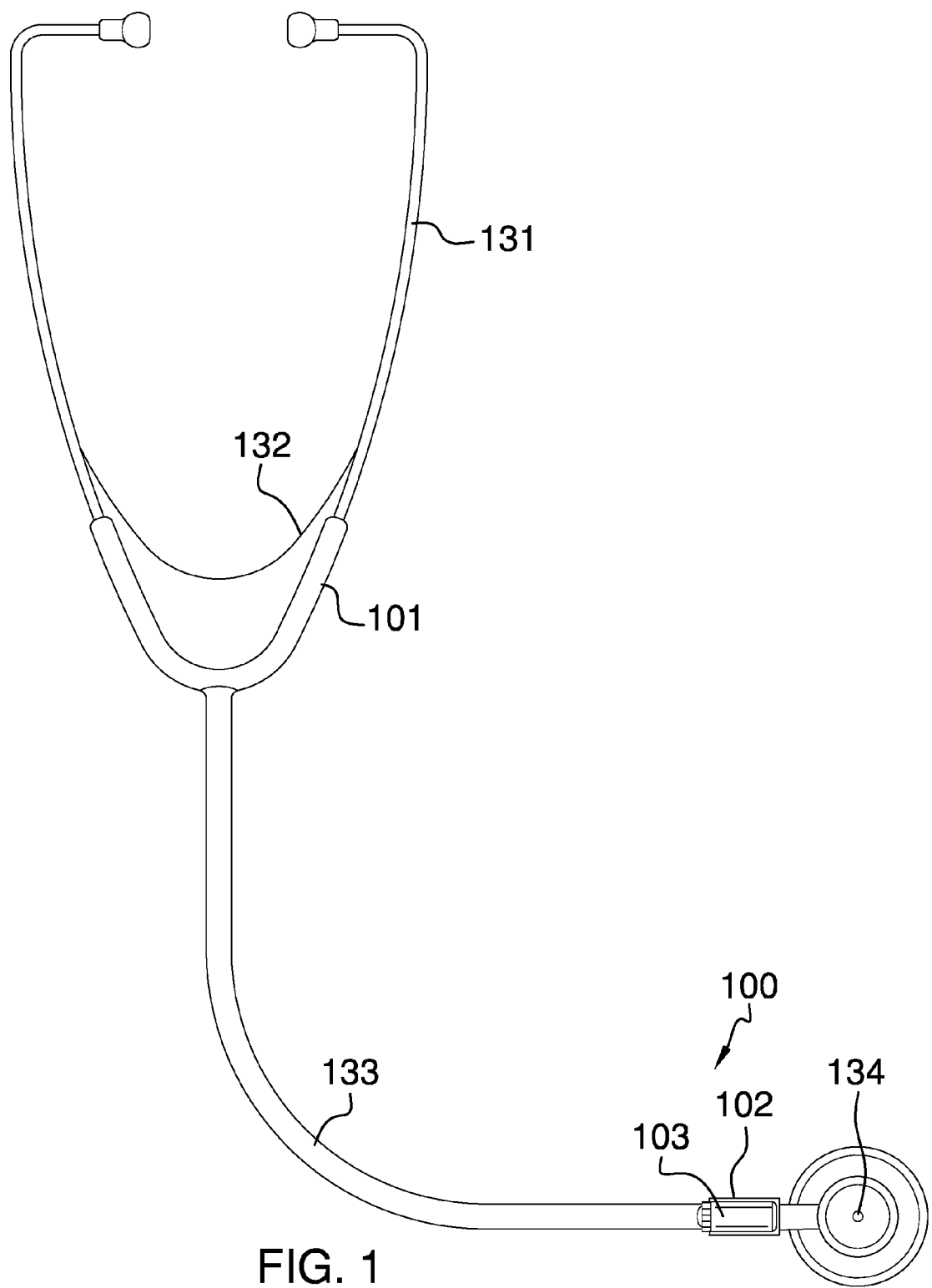
FIG. 1 is a front view of an embodiment of the disclosure.
Figure 2:
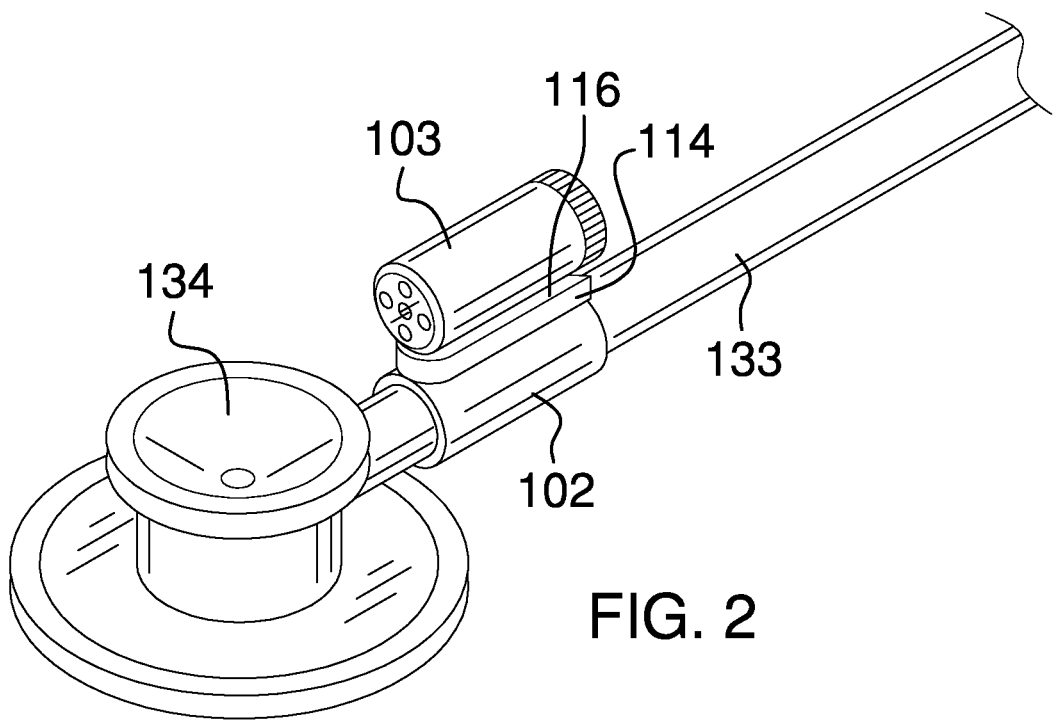
FIG. 2 is a front perspective of an embodiment of the disclosure.
Figure 3:
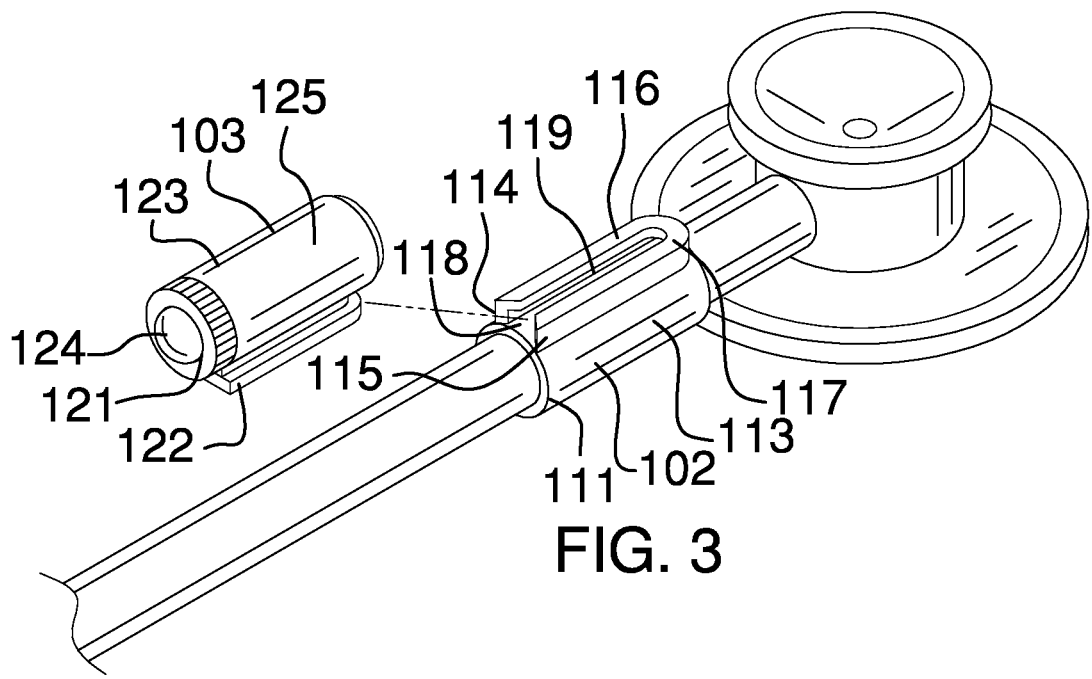
FIG. 3 is a rear perspective view of an embodiment of the disclosure.
Figure 4:
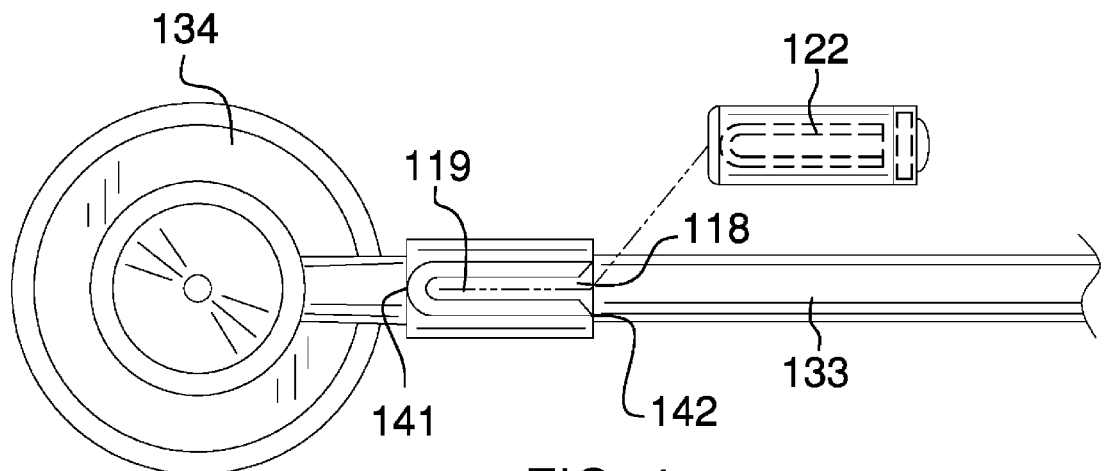
FIG. 4 is a top view of an embodiment of the disclosure.
Figure 5:
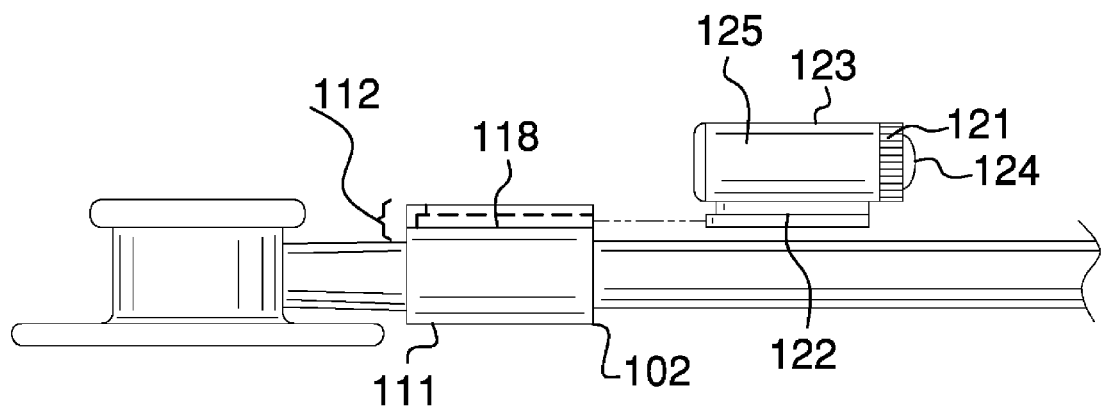
FIG. 5 is a side view of an embodiment of the disclosure.
Figure 6:
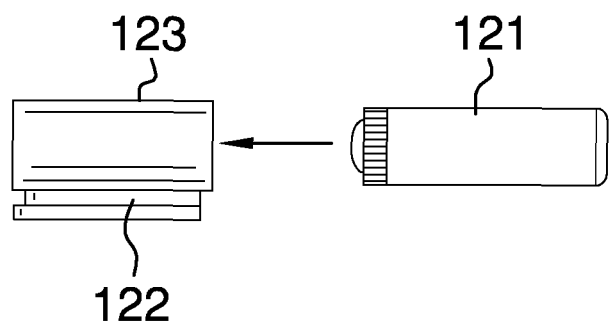
FIG. 6 is a detail view of an embodiment of the disclosure.
Figure 7:
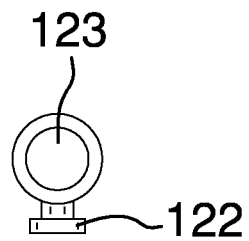
FIG. 7 is a detail view of an embodiment of the disclosure.

Detailed reference will now be made to a first potential embodiment of the disclosure, which is illustrated in FIGS. 1 through 7. The stethoscope flashlight 100 (hereinafter invention) comprises a stethoscope 101, a tube mount 102, and a flashlight 103.

The tube mount 102 is used to attach the flashlight 103 to the tube 133 of the stethoscope 101. The flashlight 103 is mounted in a manner that is readily attached or detached from the stethoscope 101. The tube mount 102 further comprises a tube cylinder 111 and a mounting bracket 112. The tube cylinder 111 is a hollow cylinder that is sized to allow the tube 133 of the stethoscope 101 to pass through the tube cylinder 111. The mounting bracket 112 is mounted on the first outer face 113 of the tube cylinder 111. The mounting bracket 112 further comprises a first wall 114, a second wall 115, and a rim 116. The mounting bracket 112 is further defined with a first end 141 and a second end 142. The first wall 114 and the second wall 115 project away from the tube cylinder 111 such that the first wall 114 and the second wall 115 project away from the tube cylinder 111 so that they are parallel to each other. The first wall 114 and the second wall 115 are joined at the first end 141 of the mounting bracket 112 to form a U shape 117. At the edge of the first wall 114 that is distal from the tube cylinder 111 is formed a rim 116 that projects perpendicularly away from the first wall 114 towards the second wall 115. The rim 116 continues as a single structure around the U shape 117 of the first end 141 to the second wall 115. At the second wall 115, the rim 116 projects perpendicularly away from the second wall 115 towards the first wall 114.

The construction of the mounting bracket 112 creates an enclosed space 118 into which a mounting shoe 122 containing the flashlight 103 can be inserted at the second end 142 of the mounting bracket 112.

The flashlight 103 further comprises a Mini LED flashlight 121, the mounting shoe 122 and a mounting cylinder 123. The mini LED flashlight 121 is selected such that the on off switch 124 is located at one of the ends of the mini LED flashlight 121. The mounting cylinder 123 is a hollow cylinder that sized to receive the mini LED flashlight 121. The mounting shoe 122 is a structure that projects away from the second outer face 125 of the mounting cylinder 123. The shape and size of the mounting shoe 122 are designed to fit within the enclosed space 118 and to project through the open area 119 defined by the rim 116.

To install the tube mount 102 on the stethoscope 101, the tube 133 of the stethoscope 101 is removed from the drum 134 and inserted through the tube cylinder 111 of the tube mount 102. The tube 133 of the stethoscope 101 is reattached to the drum 134. To attach the flashlight 103 to the tube mount 102, the mini LED flashlight 121 is inserted into the mounting cylinder 123. The mounting shoe 122 is then inserted into the enclosed space 118 defined by the mounting bracket 112.

To use the invention 100, the mini LED flashlight 121 can be turned on using the on off switch 124 while the mini LED flashlight 121 is attached to the tube 133 of the stethoscope 101 and used normally. Alternatively, the mini LED flashlight 121 can be stored within the mounting cylinder 123 removed from the mounting cylinder 123 before being turned on and used normally.

The stethoscope 101 is a commercially available stethoscope commonly used by physicians. The tube mount 102 can be formed as a single unit from molded plastic. Suitable plastics include, but are not limited to, polyethylene and polypropylene. The mounting shoe 122 and the mounting cylinder 123 can be formed as a single unit from molded plastic. Suitable plastics include, but are not limited to, polyethylene and polypropylene. The mini LED flashlight 121 is readily and commercially available.

The following definition was used in this disclosure:

Stethoscope: As used in this disclosure, a stethoscope 101 is an instrument that is used for listening to sounds within the body. A stethoscope 101 further comprises a binaural 131, a binaural spring 132, a tube 133, and a drum 134.

The following definitions and directional references were used in this disclosure:

With respect to the above description, it is to be realized that the optimum dimensional relationship for the various components of the invention described above and in FIGS. 1 through 7, include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

What is claimed is:

1. A device comprising
a tube mount and a flashlight;
wherein the device is adapted for use with a stethoscope;
wherein the tube mount is attached to the stethoscope;
wherein the flashlight mounts on the tube mount;
wherein the flashlight is mounted on the stethoscope in a manner that is readily attached or detached from the stethoscope;
wherein the tube mount further comprises a tube cylinder and a mounting bracket;
wherein the tube cylinder comprises a hollow cylinder that is sized to allow the tube of the stethoscope to pass through the tube cylinder;
wherein the mounting bracket is mounted on the first outer face of the tube cylinder;
wherein the mounting bracket further comprises a first wall, a second wall, and a rim;
wherein the mounting bracket is further defined with a first end and a second end;
wherein the first wall and the second wall project away from the tube cylinder such that they are parallel to each other;
wherein the first wall and the second wall are joined at the first end of the mounting bracket to form a U shape;
wherein at the edge of the first wall that is distal from the tube cylinder is formed said rim that projects perpendicularly away from the first wall towards the second wall.

2. The device according to claim 1 wherein said rim continues as a single structure around the U shape of the first end to the second wall.

3. The device according to claim 2 wherein at the second wall, said rim projects perpendicularly away from the second wall towards the first wall.

4. The device according to claim 3 wherein the mounting bracket creates an enclosed space.

5. The device according to claim 4 wherein said rim forms an open area.

6. The device according to claim 5 wherein the flashlight further comprises a mini LED flashlight, a mounting shoe and a mounting cylinder.

7. The device according to claim 6 wherein the mini LED flashlight is selected such that an on off switch is located at one of the ends of the mini LED flashlight.

8. The device according to claim 7 wherein the mounting cylinder is a hollow cylinder that sized to receive the mini LED flashlight.

9. The device according to claim 8 wherein the mounting shoe is a structure that projects away from the second outer face of the mounting cylinder.

10. The device according to claim 9 wherein the shape and size of the mounting shoe are designed to fit within the enclosed space and to project through the open area defined by said rim.

* * * * *